(12) United States Patent
Qian et al.

(10) Patent No.: US 11,992,407 B1
(45) Date of Patent: May 28, 2024

(54) MULTI-LAYERED COMPOSITE BIONIC SELF-RETAINING PROSTHESIS FOR FEMORAL SHAFT

(71) Applicant: Jilin University, Changchun (CN)

(72) Inventors: Zhihui Qian, Changchun (CN); Yue Lu, Changchun (CN); Jincheng Wang, Changchun (CN); Lei Ren, Changchun (CN); Hao Chen, Changchun (CN); Kunyang Wang, Changchun (CN); Kaize Wang, Changchun (CN); Guangsheng Song, Changchun (CN); Youhao Diao, Changchun (CN); Luquan Ren, Changchun (CN)

(73) Assignee: JILIN UNIVERSITY, Changchun (CN)

( * ) Notice: Subject to any disclaimer, the term of this patent is extended or adjusted under 35 U.S.C. 154(b) by 0 days.

(21) Appl. No.: 18/236,983

(22) Filed: Aug. 23, 2023

(30) Foreign Application Priority Data

Feb. 15, 2023 (CN) .......................... 202310115221.2

(51) Int. Cl.
*A61F 2/30* (2006.01)
*A61F 2/28* (2006.01)
(Continued)

(52) U.S. Cl.
CPC ................ *A61F 2/28* (2013.01); *A61L 27/06* (2013.01); *G06T 17/00* (2013.01); *A61F 2210/0076* (2013.01)

(58) Field of Classification Search
None
See application file for complete search history.

(56) References Cited

U.S. PATENT DOCUMENTS 5,211,664 A * 5/1993 Tepic ..................... A61L 31/146
623/16.11
6,280,473 B1 * 8/2001 Lemperle .............. A61F 2/2803
606/154
(Continued)

FOREIGN PATENT DOCUMENTS

CN 105796214 A * 7/2016 ............. A61F 2/442
CN 112006815 A * 12/2020
(Continued)

OTHER PUBLICATIONS

2016.*
(Continued)

*Primary Examiner* — Ann Schillinger
(74) *Attorney, Agent, or Firm* — Alston & Bird LLP

(57) ABSTRACT

Disclosed is a multi-layered composite bionic self-retaining prosthesis for a femoral shaft, including a scaffold, an upper bone plate, and a lower bone plate. An upper outer side of the scaffold is fixed to a low inner side of the upper bone plate, and a lower outer side of the scaffold is fixed to an upper inner side of the lower bone plate. The scaffold includes an upper trabeculae layer, a middle cortical bone layer and a lower trabeculae layer. The middle cortical bone layer is a multi-layered composite structure which includes an outer frame layer, a middle filling layer and an inner frame layer. The upper and lower bone plates each include an inner trabeculae layer and an outer reinforcement layer.

6 Claims, 6 Drawing Sheets

(51) Int. Cl.
 *A61F 2/44* (2006.01)
 *A61L 27/06* (2006.01)
 *G06T 17/00* (2006.01)

(56) References Cited

U.S. PATENT DOCUMENTS

| | | | | |
|---|---|---|---|---|
| 6,312,467 | B1* | 11/2001 | McGee | A61L 31/026 |
| | | | | 623/16.11 |
| 9,585,755 | B2* | 3/2017 | Rose | A61B 17/82 |
| 10,070,962 | B1* | 9/2018 | Moore | A61F 2/3609 |
| 10,631,987 | B2* | 4/2020 | Chung | A61L 27/58 |
| 10,945,845 | B2* | 3/2021 | Ricci | A61L 27/54 |
| 11,628,001 | B2* | 4/2023 | Dean | A61B 17/8071 |
| | | | | 606/286 |
| 2007/0203584 | A1* | 8/2007 | Bandyopadhyay | |
| | | | | B23K 26/0006 |
| | | | | 623/901 |
| 2008/0172095 | A1* | 7/2008 | Salerni | A61B 17/8085 |
| | | | | 606/280 |
| 2011/0076316 | A1* | 3/2011 | Sivananthan | A61P 19/02 |
| | | | | 435/395 |
| 2011/0307073 | A1* | 12/2011 | Teoh | A61L 27/56 |
| | | | | 623/23.61 |
| 2016/0262894 | A1* | 9/2016 | Cronstein | A61F 2/28 |
| 2018/0193530 | A1* | 7/2018 | Barbas | A61F 2/30767 |
| 2019/0046322 | A1* | 2/2019 | Moore | A61F 2/3859 |
| 2020/0214846 | A1* | 7/2020 | Perego | A61F 2/4014 |
| 2021/0228360 | A1* | 7/2021 | Hunt | A61F 2/2803 |
| 2021/0338454 | A1* | 11/2021 | Afzal | A61F 2/447 |
| 2023/0136789 | A1* | 5/2023 | Ruane | A61L 27/58 |
| | | | | 424/426 |

FOREIGN PATENT DOCUMENTS

| | | | | |
|---|---|---|---|---|
| CN | 113749825 | A | * | 12/2021 |
| CN | 113821848 | A | * | 12/2021 |
| CN | 215162801 | U | * | 12/2021 |
| CN | 216294354 | U | * | 4/2022 |
| DE | 102013104801 | A1 | * | 12/2013 .......... A61B 17/864 |
| EP | 1206226 | A1 | | 2/2001 |
| WO | 01/08611 | A1 | | 2/2001 |
| WO | WO-2012010327 | A1 | * | 1/2012 ............ A61B 17/70 |
| WO | 2017/063425 | A1 | | 4/2017 |
| WO | WO-2019104392 | A1 | * | 6/2019 |

OTHER PUBLICATIONS

2020.*
2021.*
2022.*
2013.*
Chinese Office Action issued on Apr. 12, 2023 for Chinese Patent Application No. 202310115221.2.

* cited by examiner

MULTI-LAYERED COMPOSITE BIONIC SELF-RETAINING PROSTHESIS FOR FEMORAL SHAFT

CROSS-REFERENCE TO RELATED APPLICATION

This patent application claims the benefit and priority of Chinese Patent Application No. 202310115221.2 filed with the China National Intellectual Property Administration on Feb. 15, 2023, the disclosure of which is incorporated by reference herein in its entirety as part of the present application.

TECHNICAL FIELD

The present disclosure belongs to the technical field of medical devices, and in particular to a multi-layered composite bionic self-retaining prosthesis for a femoral shaft.

BACKGROUND

Reconstruction of segmental bone defects caused by trauma, infection or tumor resection is a challenging clinical problem all over the world. The femoral shaft, as the longest weight-bearing backbone of human body, is the prone site of segmental bone defects. At present, the main treatment methods for segmental bone defects include autologous and allogeneic bone grafts. But due to the existence of donor-site complications, immune rejection and other problems, the therapeutic effect of patients cannot be effectively guaranteed, and it is easy to lead to deep infection, delayed healing and other clinical problems. Therefore, the development of a high-performance prosthesis for the treatment of segmental bone defect of the femoral shaft has become the focus and difficulty of orthopedic clinical research. The results of clinical investigation show that titanium and titanium alloy prosthesis have become the first choice to repair segmental bone defects of the femoral shaft due to their high biocompatibility and high corrosion resistance. However, there are still the following problems in clinical application of titanium and titanium alloy implants.

First, as most of the current implants are designed as dense or single porous structures, the ingrowth efficiency of new bone is limited, and then the stability of the implant-bone interface cannot be ensured, resulting in easy displacement of the prosthesis. In addition, although the titanium and titanium alloys have relatively good biocompatibility and mechanical properties, it is inevitable to produce stress shielding effect because their elastic modulus (100-120 GPa) is much larger than that of bones (0.02-30 GPa). The lack of stress stimulation in fracture healing or bone regeneration leads to negative bone remodeling balance, which eventually leads to serious problems such as fractures around an artificial prosthesis or aseptic loosening around the prosthesis.

Secondly, as the femur is the weight-bearing area of the lower limb, its immediate stability after operation is crucial. Therefore, after prosthesis implantation, auxiliary fixation system is often used to strengthen the mechanical strength while providing initial mechanical connection for the bone-implant interface. At present, the most common auxiliary fixation method is to use a steel plate-screw system for auxiliary fixation. However, the steel plate-screw system needs to be removed by second operation, which increases the infection rate of patients. In addition, in the process of postoperative healing, the occupation of the steel plate hinders the bone bridging between the bone defects, resulting in uneven distribution of new bone tissue on the side with the steel plate and the side without the steel plate. In this regard, some researchers have tried to use degradable materials such as calcium phosphate ceramics as auxiliary fixation plates. However, as the material mechanical strength of the calcium phosphate ceramics is lower than that of titanium and its alloys, the auxiliary fixation mechanical properties are insufficient, which may lead to fracture failure of the implant or the failure of the applied bone fixation system.

In conclusion, titanium or titanium alloy implants used to repair segmental bone defects of the femoral shaft generally have the common problems that the bone ingrowth efficiency is limited, stress shielding exists and the auxiliary fixation system hinders bone bridging and requires second operation, which need to be solved urgently.

Deep-sea glass sponges and human bone provide a new solution to these problems. The glass sponge in the deep sea has achieved excellent mechanical properties of stability, light weight, high strength and high torsion resistance by using limited self-materials to protect itself from the attack of ocean currents and other marine animals. This coincides with the goal that the ideal artificial implant should be lightweight and have excellent mechanical properties. Researches have shown that the naturally optimized bidiagonal grid support structure and heterogeneous arrangement of the glass sponge can effectively disperse stress, enhance strength, and achieve excellent flexural resistance, and thus inspiration is provided for the development of novel low elastic modulus implants. In the human bone, bone can be divided into cortical bone and cancellous bone. The cortical bone is a lamellar structure composed of organic and inorganic composite materials, which is located on the lateral of the bone to provide a solid and stable support for the bone. The cancellous bone is a loose and porous tissue inside the bone to provide a sufficient space for cell distribution and migration, waste metabolism and nutrient circulation. Thus, a new solution is provided for solving the problems of the current prosthesis that the ingrowth efficiency of the new bone is low, stress shielding is existent, and the auxiliary fixation system hinders bone bridging and requires secondary operation. Based on this, a bionic self-retaining femoral shaft prosthesis is provided, which can improve the bone ingrowth efficiency, reduce stress shielding, promote bone bridging and accelerate the healing of bone defect areas, and meanwhile, there is no need for a second operation to take out the auxiliary fixation steel plate.

SUMMARY

In order to overcome the shortcomings of the current femoral shaft prosthesis, the present disclosure provides a novel multi-layered composite bionic self-retaining prosthesis for a femoral shaft, which is mainly used for the surgical treatment of segmental bone defects of the femoral shaft. Through the composite action of a femur cortical bone-mimicking lamellar layer structure and a glass sponge-mimicking grid support structure, and combined with a design of a cancellous bone-mimicking trabecular structure at a joint of broken bone ends and an integrated design of prosthesis and bone plate, the immediate and medium long-term biomechanical stability of the prosthesis-bone interface and osseointegration efficiency after operation are effectively improved, and the healing of a bone defect area is accelerated.

To achieve the objective above, the present disclosure employs the following technical solutions.

The present disclosure is inspired according to a cortical bone lamellar structure, a cancellous bone trabeculae structure, and a deep-sea glass sponge bidiagonal structure.

Femur can be divided into cortical bone and cancellous bone. The cortical bone is located on the lateral of the bone to provide a solid and stable support for the bone. Meanwhile, the bone cortex is a lamellar structure composed of organic and inorganic composite materials, including an inner circumferential lamella and an outer circumferential lamella which are located on, and parallel to, inner and outer surfaces of the bone cortex of the backbone, and irregular interstitial lamellas arranged between the inner circumferential lamella and the outer circumferential lamella. Cancellous is an internal component of the bone, and a microstructure of the cancellous bone is composed of irregular random units called trabeculae, spacious and porous structure of which provides a space for the distribution and migration of cells as well as the flow of metabolic waste and nutrients.

Glass sponges, also known as "Venus flower baskets", are mostly found at the bottom of deep-sea mud, which are disturbed by ocean currents for a long time but is not destroyed. The research shows that the glass sponge forms a group of stable chessboard-like patterns by crossing and merging two sets of parallel diagonal bone struts into a square grid. Such a naturally optimized bidiagonal grid support structure shows excellent mechanical properties such as light weight, high strength and high torsion resistance. The strength of the structure is improved by more than 20% without additional materials, and the best structural strength performance is achieved. Meanwhile, the structure instability can be delayed to protect internal and overall integrity to the maximum extent during the bearing process.

Based on the features of a bone structure and a deep-sea glass sponge structure, a multi-layered composite bionic self-retaining prosthesis for a femoral shaft is designed, which including a scaffold, an upper bone plate, and a lower bone plate, where an upper outer side of the scaffold is fixed to a low inner side of the upper bone plate, and a lower outer side of the scaffold is fixed to an upper inner side of the lower bone plate. The scaffold includes an upper trabeculae layer, a middle cortical bone layer, and a lower trabeculae layer; the middle cortical bone layer is of a multi-layered composite structure which includes an outer frame layer, a middle filling layer, and an inner frame layer. The upper bone plate includes a first inner trabeculae layer and a first outer reinforcement layer, and the lower bone plate includes a second inner trabeculae layer and a second outer reinforcement layer. The scaffold is cylindrical; the upper bone plate and the lower bone plate are arc-shaped.

Each of the upper trabeculae layer, the lower trabeculae layer, the first inner trabeculae layer and the second inner trabeculae layer is made of a Ti—Ta alloy material.

Each of the middle cortical bone layer, the first outer reinforcement layer and the second outer reinforcement layer is made of a $Ti_6Al_4V$ material.

Compared with the current femoral shaft prosthesis, the present disclosure has the following beneficial effects.

1. Through a glass sponge-mimicking bidiagonal structure, while improving the mechanical strength of the prosthesis, the stiffness of the prosthesis is reduced, the influence of stress shielding effect is effectively reduced, and the fracture around the prosthesis or the loosening of the prosthesis are avoided.

2. Through the lamellar structure of the femur-mimicking cortical bone, and the combination of the glass sponge bidiagonal structure and a body-centered cubic structure, a high porosity and specific surface area are provided while giving consideration to the structural strength of prosthesis, so, an enough space is provided for bone cell adhesion and bone tissue formation, and efficient osteogenesis is achieved.

3. Through a trabeculae-mimicking structure, the ingrowth efficiency of new bone can be effectively improved, and a large amount of bone tissue generated in the gap between implants can provide a stable combination of the bone and the implant at a bone-implant interface, thus providing enough biological stability for the implant to replace normal bone tissue, and then achieving medium long-term physiological weight bearing after operation.

4. Through the integration of the scaffold and the bone plate, the occupation phenomenon of the bone plate can be effectively avoided, which provides a sufficient space for bone bridging between bone defects in the healing process. There is no need for a second operation to take out the bone plate, and thus the infection rate of patients is reduced. Moreover, the initial stability can be provided immediately, so as to ensure that patients can walk normally in early postoperative period.

Figure 1:
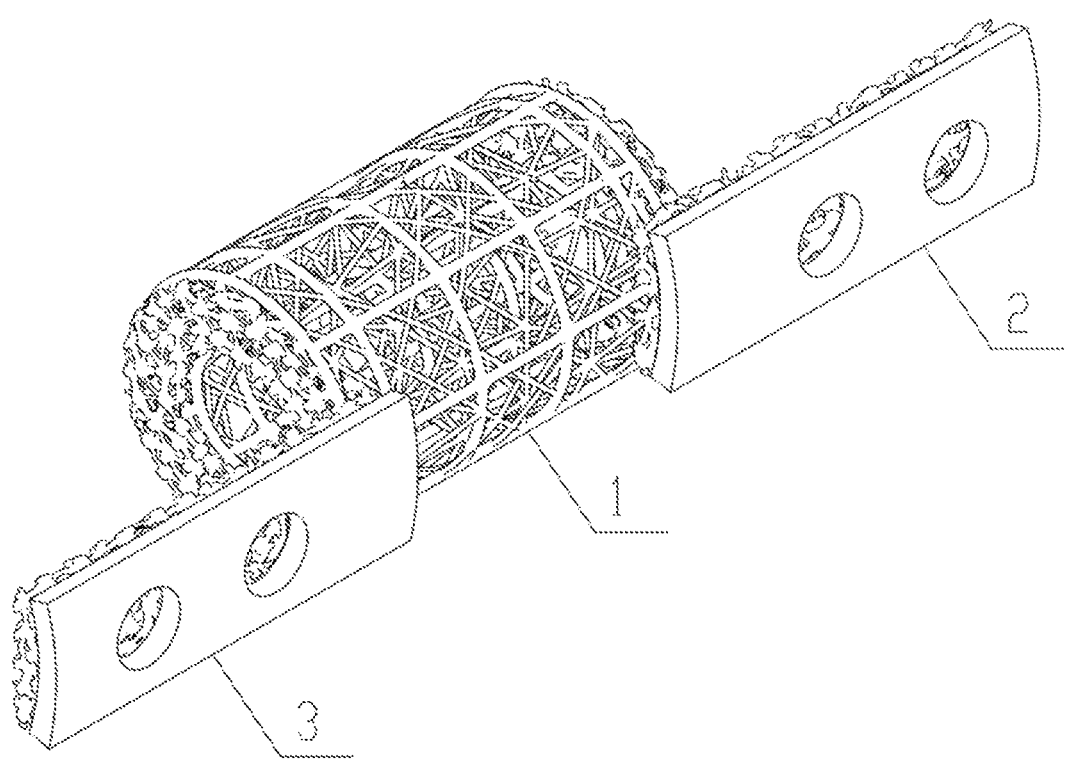
FIG. 1 is a perspective view of an overall structure according to some embodiments of the present disclosure.

In the drawings: 1 scaffold; 2 upper bone plate; 3 lower bone plate; 11 middle cortical bone layer; 12 upper trabeculae layer; 13 lower trabeculae layer; 111 outer frame layer; 112 middle filling layer; 113 inner frame layer; 21 first inner trabeculae layer; 22 first outer reinforcement layer I; 31 second inner trabeculae layer; 32 second outer reinforcement layer.

DETAILED DESCRIPTION OF THE EMBODIMENTS

As shown in FIG. 1, a multi-layered composite bionic self-retaining prosthesis for a femoral shaft includes a scaffold 1, an upper bone plate 2, and a lower bone plate 3. An upper outer side of the scaffold 1 is fixed to a low inner side of the upper bone plate 2, and a lower outer side of the scaffold 1 is fixed to an upper inner side of the lower bone plate 3. The mechanical retaining between the prosthesis and a host bone can be achieved via the upper bone plate 2 and the lower bone plate 3, which can prevent the prosthesis from displacing while providing initial postoperative mechanical stability.

Figure 2:
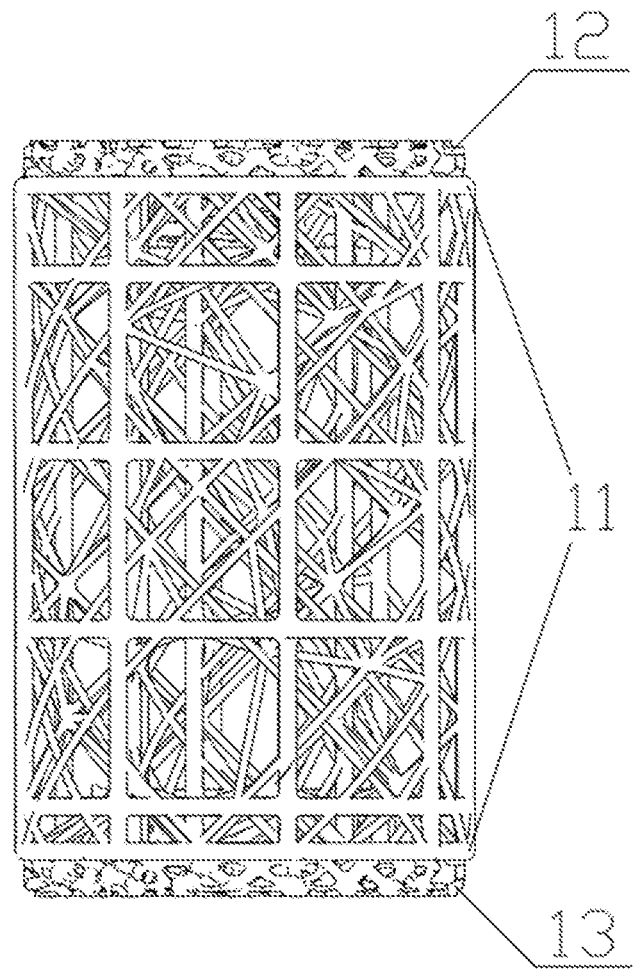
FIG. 2 is a perspective view of a scaffold structure according to some embodiments of the present disclosure.

As shown in FIG. 2, the scaffold 1 includes an upper trabeculae layer 12, a middle cortical bone layer 11, and a lower trabeculae layer 13. The upper trabeculae layer 12 and the lower trabeculae layer 13 are both a trabeculae-mimicking random porous structure. In this embodiment, the random porous structure is designed using a Voronoi-Tessellation method, and the porosity of the random porous structure ranges from 50% to 90% according to the porosity of cancellous bone of the human body, preferably from 60% to 80%, and the pore size of the random porous structure is from 500 μm to 700 μm. The upper trabeculae layer 12 and the lower trabeculae layer 13 can improve the ingrowth efficiency of new bone after the prosthesis is implanted into the host bone, and then achieve the biomechanical interlocking stability at a prosthesis-bone interface.

The Voronoi-Tessellation method is a Thiessen Polygon algorithm.

Figure 3:
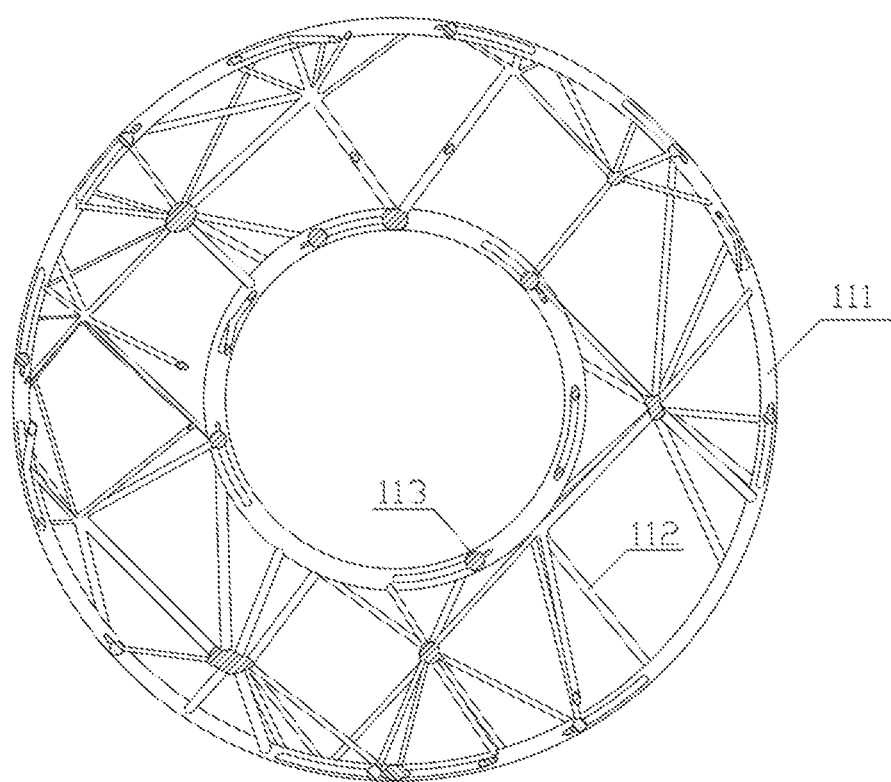
FIG. 3 is a front cross-sectional view of a scaffold according to some embodiments of the present disclosure.
Figure 4:
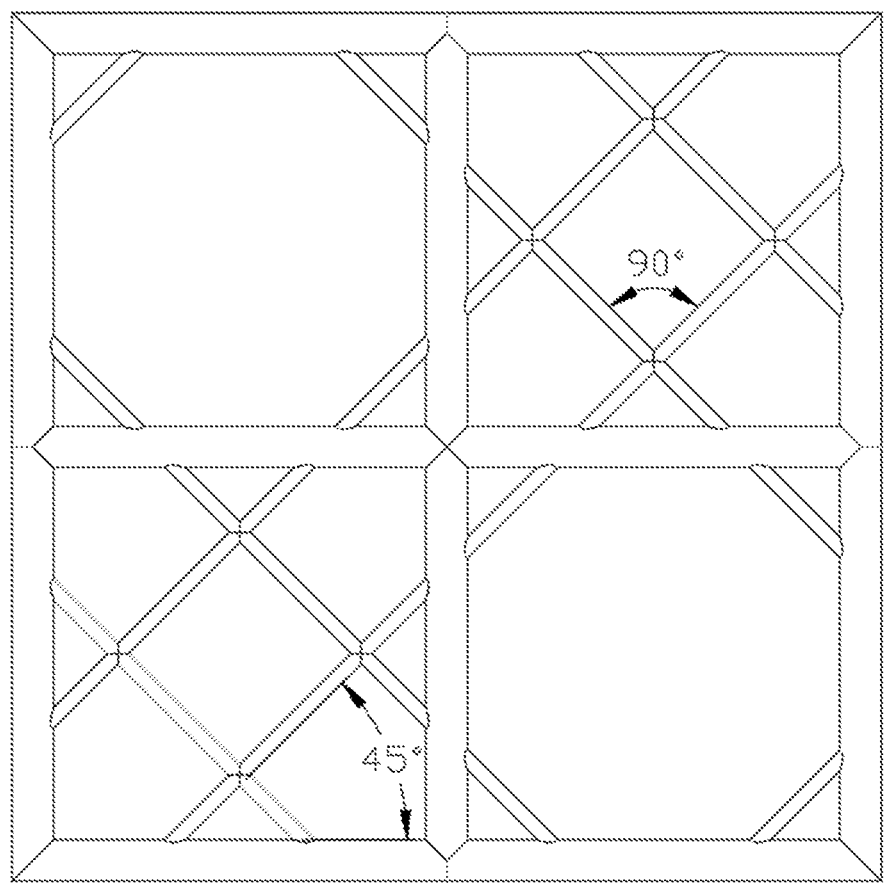
FIG. 4 is a perspective view of a glass sponge-mimicking bidiagonal structure according to some embodiments of the present disclosure.
Figure 5:
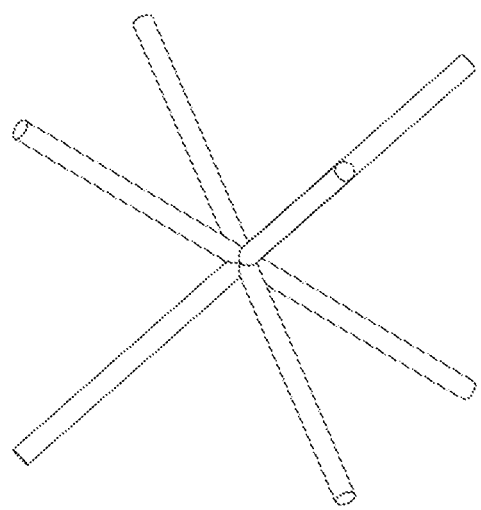
FIG. 5 is perspective view of a body-centered cubic structure according to some embodiments of the present disclosure.

As shown in FIG. 3, FIG. 4 and FIG. 5, the middle cortical bone layer 11 is a cortical bone-mimicking multi-layered composite structure includes an outer frame layer 111, a middle filling layer 112, and an inner frame layer 113, and has a hollow interior. A cell structure of each of the outer frame layer 111 and the inner frame layer 113 is a glass sponge-mimicking bidiagonal grid structure. A cell structure of the middle filling layer 112 is a body-centered cubic structure. In this embodiment, an angle of intersection θ1 between two diagonal lines of the glass sponge-mimicking structure is equal to 90°, and an angle of intersection θ2 between each of the two diagonal lines and a sideline of the square is equal to 45°. The porosity of the outer frame layer 111 and the inner frame layer 113 is from 70% to 90%. The purpose of choosing high porosity is to provide a relatively sufficient space for waste metabolism and nutrient flow in the scaffold and vascularization, and the porosity of the middle filling layer 112 is from 60% to 70%. The reason that the porosity of the middle filling layer 112 is smaller than that of the outer frame layer 111 and the inner frame layer 113 is that the femur, as the weight-bearing bone of the lower limb, requires sufficient biomechanical strength for the backbone prosthesis. The body-centered cubic structure can effectively reduce the stress shielding phenomenon while taking into account the biomechanical strength by combining with the porosity from 60% to 70%.

Figure 6:
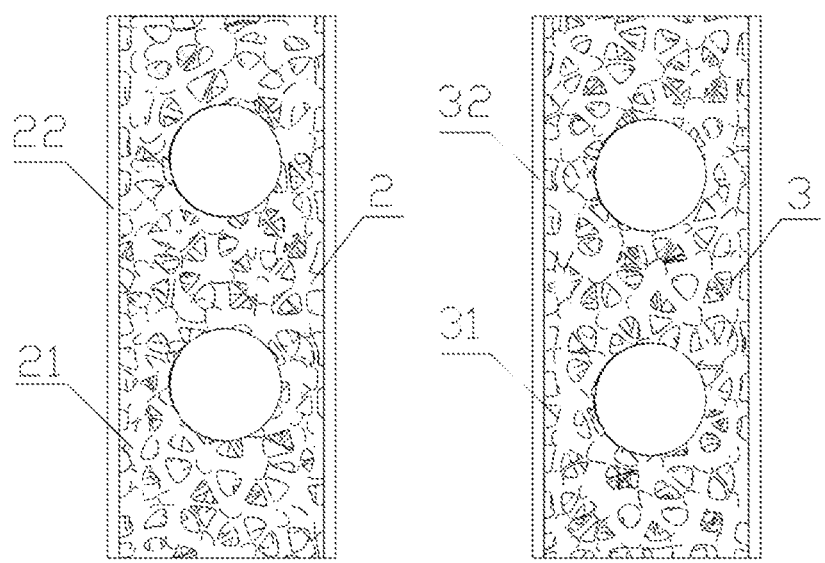
FIG. 6 is a front view of a bone plate according to some embodiments of the present disclosure.
Figure 7:
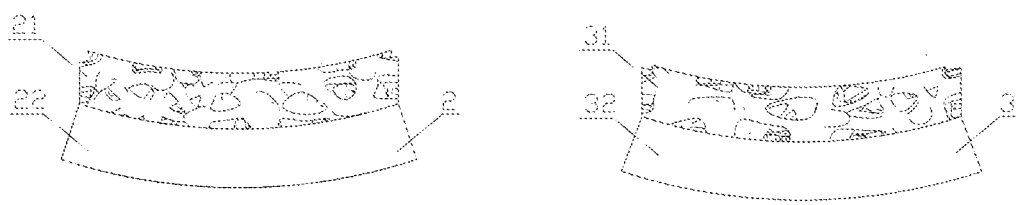
FIG. 7 is a side view of a bone plate according to some embodiments of the present disclosure.

As shown in FIG. 6 and FIG. 7, the upper bone plate 2 includes a first inner trabeculae layer 21 and a first outer reinforcement layer 22. The lower bone plate 3 includes a second inner trabeculae layer 31 and a second outer reinforcement layer 32. ⅓ and ⅔ of a length of each of the upper bone plate 2 and the lower bone plate 3 are each provided with a circular screw hole for providing a mounting position for a screw, so as to fix the prosthesis to the bone defect, thus avoiding poor recovery caused by the displacement of the prosthesis. The purpose of adopting an integrated double bone plate is to reduce the occupation of the bone plate on the prosthesis, so as to provide a sufficient space for bone bridging. In this embodiment, each of the first inner trabeculae layer 21 and the second inner trabeculae layer 31 is a random porous structure designed using a Voronoi-Tessellation method, the porosity of the first inner trabeculae layer 21 and the second inner trabeculae layer 31 ranges from 50% to 90% according to the porosity of cancellous bone of the human body, preferably from 60% to 80%, and the pore size is from 500 μm to 700 μm, so as to promote osseointegration. The first outer reinforcement layer 22 and the second outer reinforcement layer 32 are dense and nonporous, so as to ensure the biomechanical strength of the bone plate.

In this embodiment, the scaffold 1 is cylindrical.

In this embodiment, the upper bone plate 2 and the lower bone plate 3 are arc-shaped.

In this embodiment, each of the upper trabeculae layer 12, the lower trabeculae layer 13, the first inner trabeculae layer 21 and the second inner trabeculae layer 31 is made of a Ti—Ta alloy material, which can improve the efficiency of adhesion, proliferation and differentiation of bone cells and further stimulate bone regeneration.

In this embodiment, each of the middle cortical bone layer 11, the first outer reinforcement layer 22 and the second outer reinforcement layer 32 is made of a $Ti_6Al_4V$ material.

The invention claimed is:

1. A multi-layered composite bionic self-retaining prosthesis for a femoral shaft, comprising:
   a scaffold, an upper bone plate, and a lower bone plate, wherein:
   an upper outer side of the scaffold is fixed to a low inner side of the upper bone plate, and a lower outer side of the scaffold is fixed to an upper inner side of the lower bone plate;
   the scaffold comprises an upper trabeculae layer, a middle cortical bone layer, and a lower trabeculae layer; the middle cortical bone layer is of a multi-layered composite structure which comprises an outer frame layer, a middle filling layer, and an inner frame layer;
   the upper bone plate comprises a first inner trabeculae layer and a first outer reinforcement layer, and the lower bone plate comprises a second inner trabeculae layer and a second outer reinforcement layer;
   the scaffold is cylindrical;
   the upper bone plate and the lower bone plate are arc-shaped;
   a cell structure of the middle filling layer is of a body-centered cubic structure, with a porosity from 60% to 70%; and
   a cell structure of each of the outer frame layer and the inner frame layer is of a glass sponge-mimicking bidiagonal structure, with a porosity from 70% to 90%.

2. The multi-layered composite bionic self-retaining prosthesis for a femoral shaft according to claim 1, wherein each of the upper trabeculae layer, the lower trabeculae layer, the first inner trabeculae layer and the second inner trabeculae layer is of a random porous structure designed using a Voronoi-Tessellation method, a porosity of the random porous structure is from 50% to 90%, and a pore size of the random porous structure is from 500 μm to 700 μm.

3. The multi-layered composite bionic self-retaining prosthesis for a femoral shaft according to claim 2, wherein the porosity of the random porous structure is from 60% to 80%.

4. The multi-layered composite bionic self-retaining prosthesis for a femoral shaft according to claim 1, wherein ⅓ and ⅔ of a length of each of the upper bone plate and the lower bone plate are each provided with a circular screw hole for providing a mounting position for a screw, to fix the prosthesis to a bone defect to avoid poor recovery caused by prosthesis displacement.

5. The multi-layered composite bionic self-retaining prosthesis for a femoral shaft according to claim 1, wherein each of the upper trabeculae layer, the lower trabeculae layer, the first inner trabeculae layer and the second inner trabeculae layer is made of a Ti—Ta alloy material.

6. The multi-layered composite bionic self-retaining prosthesis for a femoral shaft according to claim 1, wherein each of the middle cortical bone layer, the first outer reinforcement layer and the second outer reinforcement layer is made of a $Ti_6Al_4V$ material.

\* \* \* \* \*